United States Patent
Mullen

(10) Patent No.: US 6,238,341 B1
(45) Date of Patent: May 29, 2001

(54) ULTRASOUND PROBE HAVING INTEGRATED USER-OPERABLE FUNCTION SWITCH

(75) Inventor: Paul Mullen, Waukesha, WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/221,969

(22) Filed: Dec. 28, 1998

(51) Int. Cl.[7] ........................................ A61B 8/00
(52) U.S. Cl. ............................. 600/437; 600/458
(58) Field of Search ................... 600/459, 460, 600/458, 437, 461

(56) References Cited

U.S. PATENT DOCUMENTS 5,351,692 * 10/1994 Dow et al. ........................ 600/459
5,505,203 * 4/1996 Deitrich et al. ................... 600/459

* cited by examiner

Primary Examiner—Marvin M. Lateef
Assistant Examiner—Maulin Patel
(74) Attorney, Agent, or Firm—Dennis M. Flaherty; Christian G. Cabou; Phyllis Y. Price

(57) ABSTRACT

An ultrasound probe having an integrated user-operable switch mechanism with two or more positions for respectively requesting activation of a single function or multiple functions. For example, the user-operable switch mechanism may be of the type having only "on" and "off" positions. In response to movement (e.g., by depression, rotation or sliding) of the switch to the "on." position, the system host computer will activate the associated system function in accordance with the current order of prioritized tasks to be performed. For example, the switch could be mapped to a freeze or print function. Alternatively, the user-operable switch may be of the type having multiple positions (e.g., a sliding switch or a rotary switch) corresponding to multiple functions.

21 Claims, 3 Drawing Sheets

ULTRASOUND PROBE HAVING INTEGRATED USER-OPERABLE FUNCTION SWITCH

FIELD OF THE INVENTION

This invention generally relates to the operator interface of an ultrasound imaging system. In particular, the invention relates to means for operator input of commands for controlling the system modes of operation and for setting selectable system parameters.

BACKGROUND OF THE INVENTION

Conventional ultrasound imaging systems are capable of operating in any one of a plurality of modes. The most common modes of diagnostic ultrasound imaging include B- and M-modes (used to image internal, physical structure), and the Doppler and color flow modes (the latter two being primarily used to image flow characteristics, such as in blood vessels). In conventional B-mode imaging, ultrasound scanners create images in which the brightness of a pixel is based on the intensity of the echo return. The color flow mode is typically used to detect the velocity of fluid flow toward/away from the probe, and it essentially utilizes the same technique as is used in the Doppler mode. Whereas the Doppler mode displays velocity versus time for a single selected sample volume, color flow mode displays hundreds of adjacent sample volumes simultaneously, all superimposed on a B-mode image and color-coded to represent each sample volume's velocity.

Conventional ultrasound imaging systems provide a two-dimensional image representing the biological tissue in a plane scanned by a probe. A three-dimensional volume can be imaged by moving the probe so that scanning occurs in a succession of scan planes, each scan producing a respective image frame of acquired data.

The probe is typically configured to be held in the hand of the sonographer. A typical probe comprises a transducer array seated in the distal end of a probe housing and an electrical cable penetrating the proximal end of the probe housing. The cable comprises a multiplicity of coaxial wires which connect the elements of the transducer array to the receive channels of the beamformer via a probe/system connector. A conventional transducer array comprises a multiplicity of transducer elements made of piezo-electric material. Typically, each transducer element has metallic coatings on opposing front and back faces to serve as ground and signal electrodes respectively. The signal electrodes are typically connected to respective electrical conductors formed on one or more flexible printed circuit boards (PCBs). The flexible PCBs are in turn electrically coupled to the coaxial wires of the probe cable.

By selecting the time delay (or phase) and amplitude of the voltages applied to the transducer elements, ultrasonic waves can be transmitted which combine to form a net ultrasonic wave that travels along a preferred vector direction and is focused at a selected point along the beam. The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element. A single scan line (or small localized group of scan lines) is acquired by transmitting focused ultrasound energy at a point in the region of interest and then receiving the reflected energy over time.

In the B-mode, for example, the ultrasound image is composed of multiple image scan lines. The brightness of a pixel is based on the intensity of the echo return from the biological tissue being scanned. The outputs of the receive beamformer channels are coherently summed to form a respective pixel intensity value for each sample volume in the object region or volume of interest. These pixel intensity values are log-compressed and scan-converted to form an image frame of pixel data which can be displayed on a monitor. Multiple scans are performed in succession and multiple image frames are displayed at the acoustic frame rate on the display monitor.

In the case where the sonographer is manipulating the transducer probe by hand, one hand is used to control the position of the probe relative to the patient while the other hand is used as necessary to operate levers and keys on the control panel. For example, if the sonographer wishes to freeze or print the ultrasound image currently being displayed on the monitor, the sonographer depresses a "freeze" or "print" button on the control panel with his free hand. There is a need for an operator interface which is located to reduce the operator movements required to perform ultrasound examination.

SUMMARY OF THE INVENTION

The present invention is an ultrasound probe having an integrated user-operable input device with two or more positions for respectively requesting activation of a single function or multiple functions or for setting a system parameter. For example, the user-operable input device may be a switch mechanism of the type having only "on" and "off" positions. In response to movement (e.g., by depression, rotation or sliding) of the switch to the "on" position, the system host computer will activate the associated system function in accordance with the current order of prioritized tasks to be performed. For example, the switch could be mapped to a freeze or print function. Alternatively, the user-operable switch may be of the type having multiple positions (e.g., a sliding switch or a rotary switch) corresponding to multiple functions. In the case of multiple-function switches, the positions may indicate variable levels of a parameter or the selection of a function or combination of functions. The switch may also be implemented as a continuously variable device such as a potentiometer, touch pad or encoder. In this implementation the mechanism may represent the selection of a variable parameter such as ultrasound receiver gain, dynamic range or Doppler velocity scale.

Preferably the switch is mounted on the probe at an ergonomically acceptable location. For example, the switch could placed at a location which is readily depressed by the thumb of the hand holding the probe. The incorporation of this switch in an ultrasound probe will reduce operator movements required to perform ultrasound examinations.

DETAILED DESCRIPTION OF THE PREFERRED EMBODIMENTS

Figure 1:
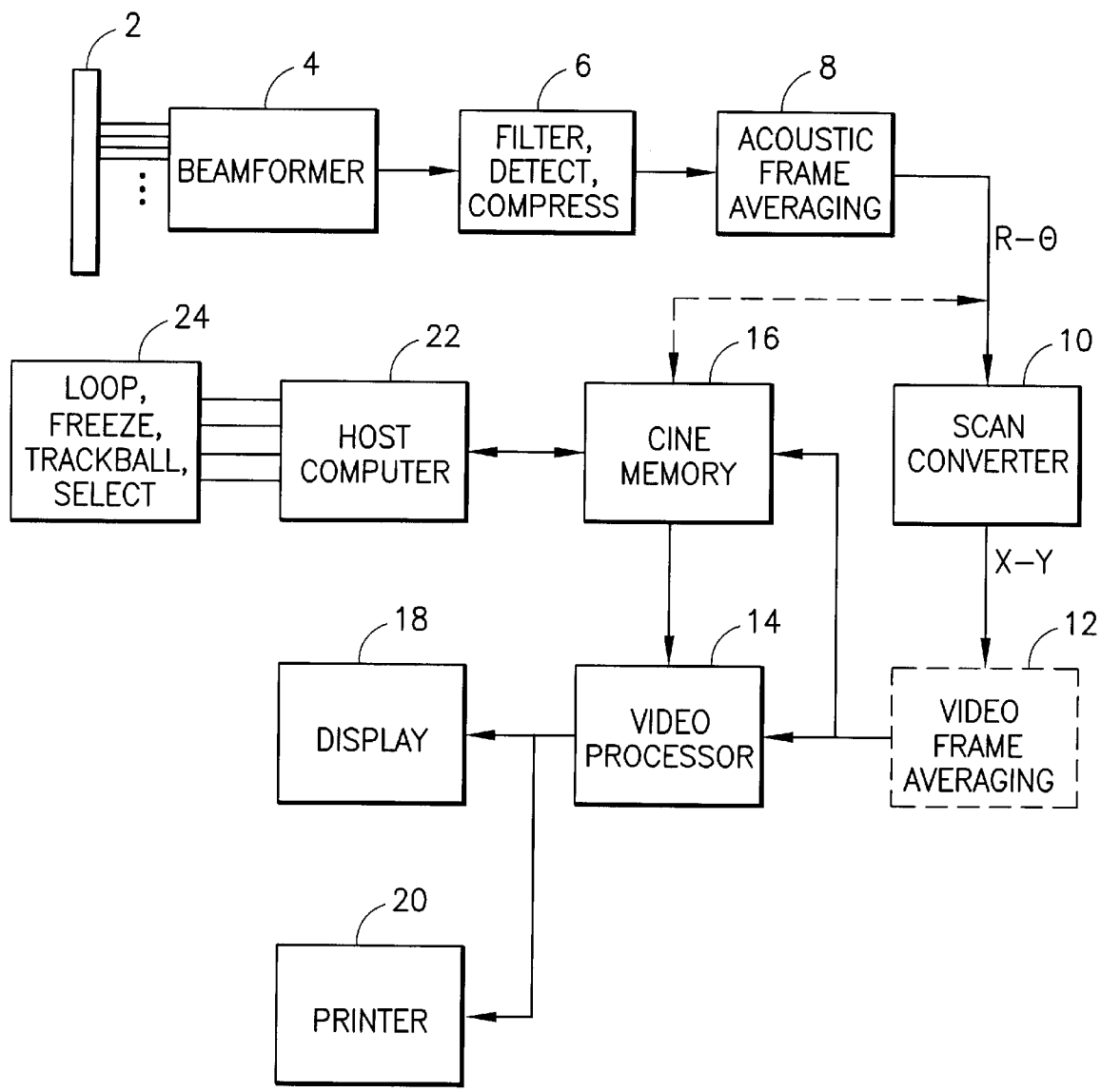
FIG. 1 is a block diagram of a typical ultrasound imaging system.

The basic signal processing chain for a conventional ultrasound imaging system is depicted in FIG. 1. An ultrasound transducer array 2 is activated to transmit an acoustic burst along a scan line. The return RF signals are detected by the transducer elements and then formed into a receive beam by the beamformer 4. The beamformer output data (I/Q or RF) for each scan line is passed through a processing chain 6 which, for the B-mode, includes equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. The frame averaging may be implemented by an FIR or an IIR filter. In general, the compressed images are in R-$\theta$ format (for a sector scan), which is converted by the scan converter 10 into X-Y format for video display. on some systems, frame averaging may be performed on the video X-Y data (indicated by dashed block 12) rather than the acoustic frames before scan conversion, and sometimes duplicate video frames may be inserted between acoustic frames in order to achieve a given video display frame rate. The video frames are passed on to a video processor 14, which basically maps the video data to a gray map for video display on a display monitor 18. A gray-mapped image frame from video processor 14 can also be printed out on a printer 20.

System control is centered in a host computer 22, which accepts operator inputs through an operator interface 24 (e.g., a control panel) and in turn controls and synchronizes the various subsystems. (In FIG. 1, only the image data transfer paths are depicted.) During B-mode imaging, a long sequence of the most recent images are stored and continuously updated automatically in a cine memory 16. Some systems are designed to save the R-$\theta$ acoustic images (this data path is indicated by the dashed line in FIG. 1), while other systems store the X-Y video images. The image loop stored in cine memory 16 can be reviewed via track-ball control, and a section of the image loop can be selected for hard disk storage. For an ultrasound scanner with free-hand three-dimensional imaging capability, the selected image sequence stored in cine memory 16 is transferred to the host computer 22 for three-dimensional reconstruction. The result is written back into another portion of the cine memory, from where it is sent to the display system 18 via video processor 14. In addition, the host computer may be programmed to control various operating parameters as a function of the current frame (or latest sequence of frames) of video X-Y data. This is accomplished by freezing the current image frame of data via the user control panel, analyzing the data and then setting the appropriate system parameters in accordance with an adaptive algorithm. When adaptive parameter optimization is complete, the user unfreezes the display via the control panel.

Figure 2:
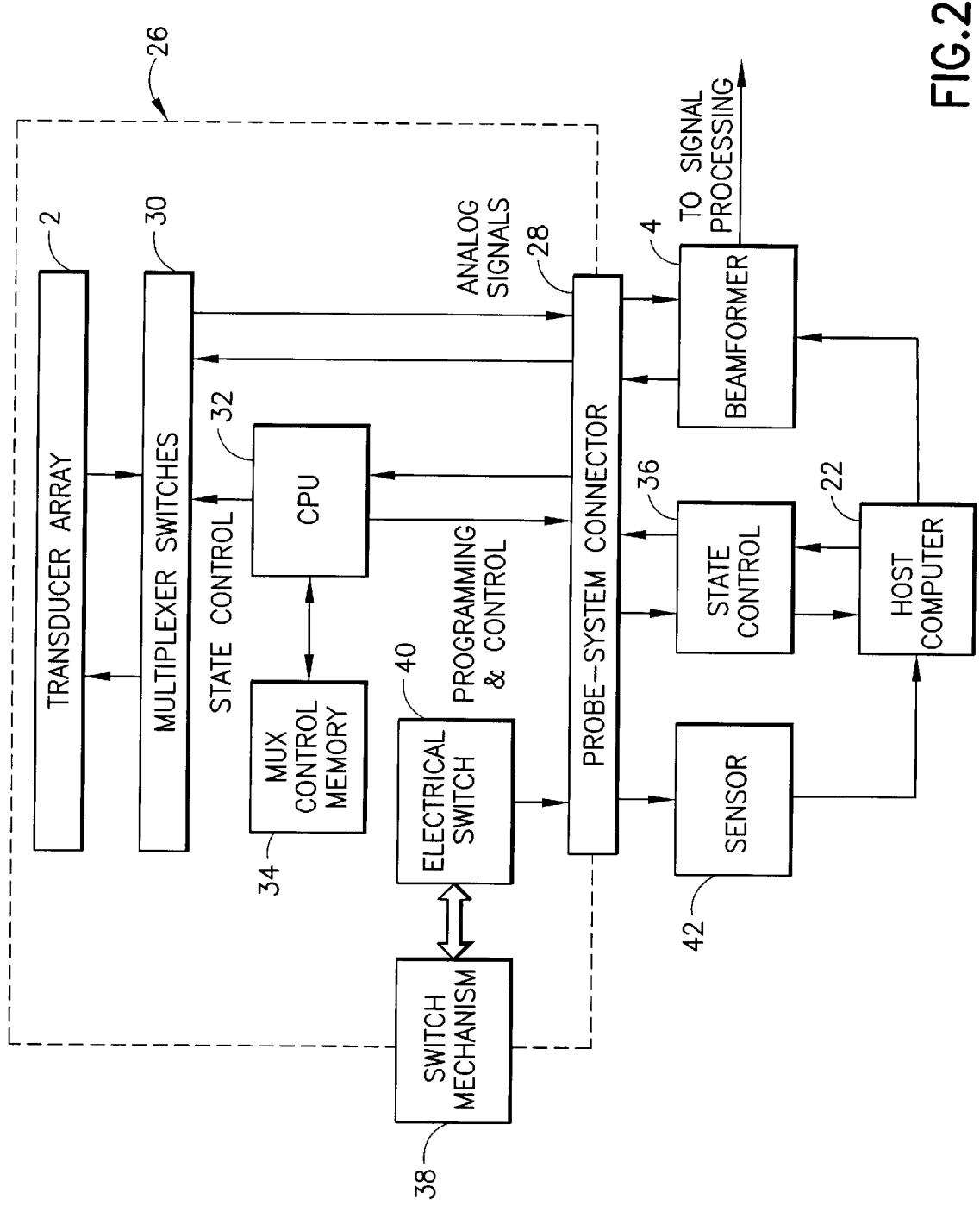
FIG. 2 is a block diagram showing a transducer probe with user-operable switch connected to an ultra-sound imaging system in accordance with a preferred embodiment of the invention.

Referring to FIG. 2, a probe 26 (generally indicated by the dashed rectangle) is connected to the imaging system by means of a probe/system connector 28. In the transmit mode, respective analog transmit waveforms are sent from the transmitter of beamformer 4 to respective elements of the transducer array 2 via respective switches of a multiplexer 30 and via respective electrical connections incorporated in the probe/system connector 28. Similarly, in the receive mode, respective analog receive signals representing ultrasound echoes detected by the elements of the transducer array 2 are sent to respective receive channels of beamformer 4 via the multiplexer 30 and the probe/system connector 28. The time delays and other beamforming parameters are changed by the host computer 22 to correspond to the multiplexer state for each image vector acquired. Also, the same multiplexer hardware may be used to scan the active aperture across the array.

The state of multiplexer 30 is controlled by a central processing unit (CPU) 32 incorporated in the probe. The MUX control data is stored in a MUX control memory 34, also incorporated in the probe. A MUX State control signal, which configures the probe with a desired aperture, is output by the host computer 22 to a state control device 36. In response to the MUX State control signal, the state control device 36 sets a register on the probe/system connector 28. The CPU 32 reads that register to determine the desired MUX State and then retrieves the MUX control data corresponding to that state from memory 34. The switches of multiplexer 30 are then set by the CPU.

In accordance with one preferred embodiment of the invention, the transducer probe has an integrated switch which can be operated by the user to implement one or more preselected functions, e.g., freezing or printing a copy of the image frame currently being displayed. The switch comprises a mechanical element or mechanism 38 and an electrical switch 40, both of which are incorporated in the probe. The electrical switch 40 is electrically connected to a switch state sensor 42 in the imaging system via the probe/system connector 28. In response to appropriate operation of the mechanism 38 by the sonographer, the switch state sensor 42 detects a change in state of the electrical switch 40 and outputs a corresponding control signal to the host computer 22. The host computer then activates or de-activates the appropriate function in accordance with the current order of prioritized tasks to be performed.

As depicted in FIG. 2, the integrated switch 38/40 is mounted on the probe 26. The switch mechanism 38 may take any one of several different forms. For example, it may take the form of a rocker switch, pushbutton switch, rotary switch, sliding switch, joystick or touch pad. The switch may have two or more positions. In the case of a single-function, two-position switch, the positions may indicate "ON" and "OFF" or similar binary selections. In the case of multiple-function switches, the positions may indicate variable levels of a parameter or the selection of a function or combination of functions. The switch 38/40 may also be implemented as a continuously variable device such as a potentiometer, touch pad or encoder. In this implementation the mechanism may represent the selection of a variable parameter such as ultrasound receiver gain, dynamic range or Dopplervelocity scale.

Although the switch of the disclosed preferred embodiment is of the mechanical type, in accordance with alternative preferred embodiments the switch activator may be non-mechanical. For example, the state of the electrical switch could be changed in response to receipt of an electrical signal (in contrast to movement of a mechanism) output by a heat-or contact-sensitive transducer situated on the exterior of the probe.

Returning to the preferred embodiment shown in FIG. 2, the electrical switch 40 preferably comprises an electrical contact (not shown) which is mechanically linked to mechanism 38. For example, for a single-function switch, the electrical contact may be constructed to bridge a pair of switch terminals inside the electrical switch 40, one switch terminal being connected by one electrical conductor to one terminal of a first electrical connector in probe/system connector 28 and the other switch terminal being connected by another electrical conductor to one terminal of a second electrical connector in probe/system connector 28. The other terminals of the first and second electrical connectors in probe/system connector 28 are respectively connected to a detecting circuit inside the switch state sensor 42. When the electrical switch 40 is closed, a closed circuit across two terminals of the detecting circuit will produce a signal at a third terminal of the detecting circuit, from which the control signal sent to the host computer is derived.

In the case of a multi-function switch, the single electrical switch 40 is supplemented by one or more additional electrical switches, the total number of electrical switches equaling the number of functions. Similarly, the switch state sensor may incorporate multiple detecting circuits to detect the changes in state of the multiple electrical, the outputs of the multiple detecting circuits being connected in parallel to the switch state sensor output. In a further alternative, multiple switch mechanisms can be movably mounted on the probe, each mechanism controlling the state of a respective one of the multiple electrical switches.

Figure 3:
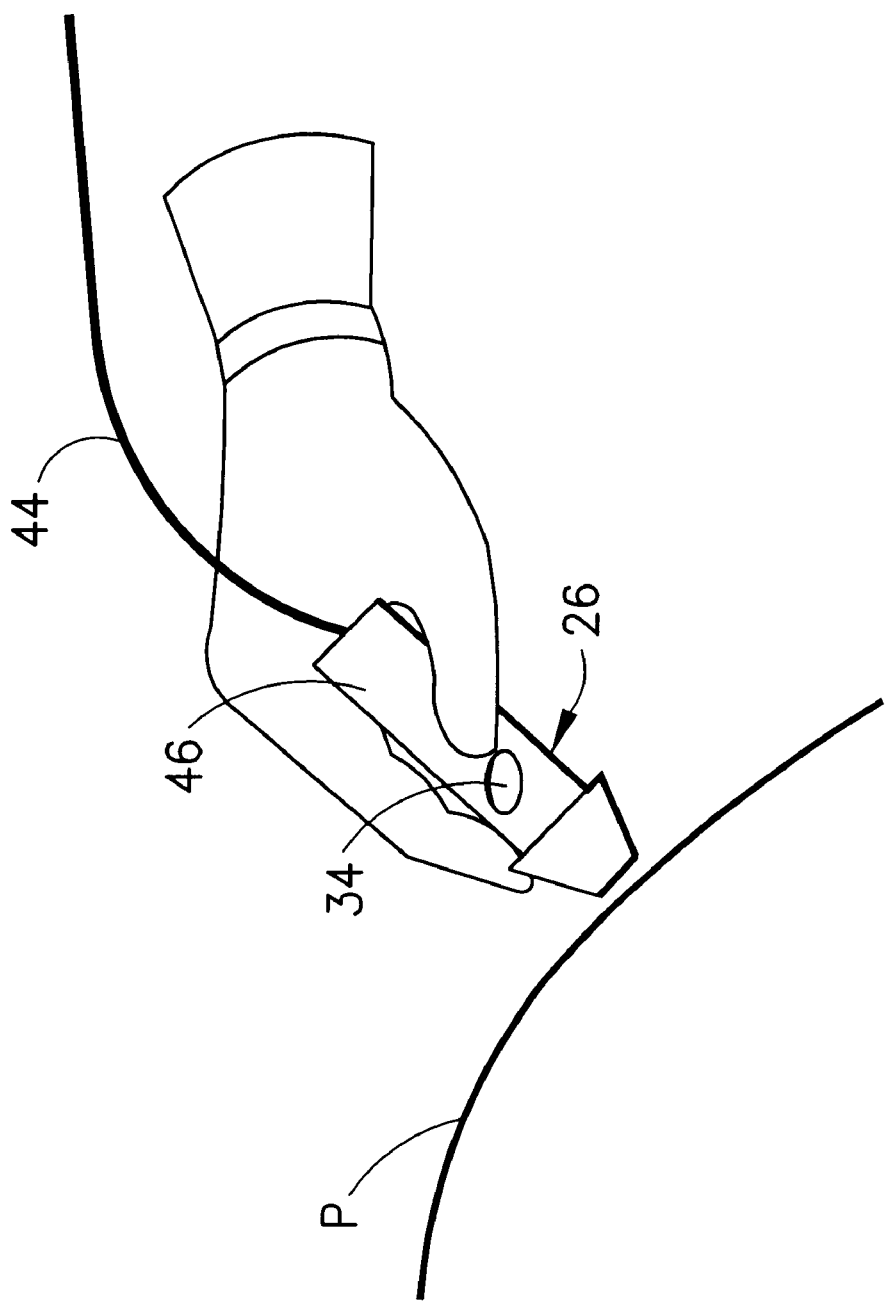
FIG. 3 is a schematic depicting a hand-held transducer probe in accordance with the preferred embodiment.

FIG. 3 generally depicts a transducer probe 26 being held in the hand of an operator while being pointed at a patient P. The reference numeral 44 indicates the probe cable, while the reference numeral 46 indicates the probe housing. The probe cable 44 comprises a multiplicity of coaxial wires for electrically coupling the transducer array elements to respective switches of the multiplexer, which is preferably mounted on a printed circuit board located near the probe/system connector. One or more of the coaxial wires is dedicated to connecting respective user-operable electrical switches to the probe/system connector. The switch mechanism is mounted so that it either protrudes outside the probe housing 46 or is accessible through an opening in the probe housing. Preferably the switch mechanism 38 is movably mounted on the probe at an ergonomically acceptable location. For example, the switch could be placed at a location which is readily depressed by the thumb or index finger of the operator, as seen in FIG. 3.

The foregoing preferred embodiment has been disclosed for the purpose of illustration. variations and modifications will be readily apparent to persons skilled in the art. For example, whether the multiplexer is incorporated in the system or in the probe is not important to practice of the present invention. All such variations and modifications are intended to be encompassed by the claims set forth hereinafter.

What is claimed:

1. A system comprising:
   an ultrasound transducer probe comprising an array of piezoelectric transducer elements and a user-operable switch operable to transition between first and second states; and
   an ultrasound imaging system electrically coupled to said probe and comprising:
   means for pulsing said transducer array to transmit ultrasound beams;
   means for forming receive beams of acoustic data derived from echo signals detected by the transducer array subsequent to said beam transmits;
   signal processing means for converting said acoustic data into a respective set of imaging data for each successive scan;
   means for displaying an image for each scan which is a function of said respective set of imaging data; and
   means for performing a function on a selected set of imaging data in response to a transition from said first state to said second state of said user-operable switch.

2. The system as recited in claim 1, wherein said function is freezing said selected set of imaging data on said displaying means.

3. The system as recited in claim 1, further comprising a memory for storing imaging data, wherein said function is storing said selected set of imaging data in said memory.

4. The system as recited in claim 1, further comprising a printer for printing imaging data, wherein said function is printing said selected set of imaging data.

5. The system as recited in claim 1, wherein said user-operable switch comprises:
   a switch mechanism movable relative to said probe housing between first and second positions; and
   an electrical switch operatively coupled to said switch mechanism, said electrical switch having a first state when said switch mechanism is in said first position and a second state when said switch mechanism is in said second position.

6. An ultrasound probe comprising:
   a probe housing;
   an ultrasound transducer array seated in said probe housing;
   a switch mechanism movable relative to said probe housing between first and second positions;
   a first electrical switch operatively coupled to said switch mechanism, said first electrical switch having an first state when said switch mechanism is in said first position and a second state when said switch mechanism is in said second position; and
   an electrical cable comprising a multiplicity of electrical conductors, a first of said electrical conductors being connected to said first electrical switch,
   wherein said switch mechanism is further movable between said first position and a third position, further comprising a second electrical switch operatively coupled to said switch mechanism, said second electrical switch having a first state when said switch mechanism is in said first position and a second state when said switch mechanism is in said third position, a second of said electrical conductors of said cable being connected to said second electrical switch.

7. A system comprising an ultrasound probe connected to an ultrasound imaging system by a probe/system connector comprising a multiplicity of electrical connections, wherein said probe comprises
   a probe housing;
   an ultrasound transducer array seated in said probe housing;
   a switch mechanism movable relative to said probe housing between first and second positions;
   a first electrical switch operatively coupled to said switch mechanism, said first electrical switch having a first state when said switch mechanism is in said first position and a second state when said switch mechanism is in said second position; and
   an electrical cable extending outside said probe housing and comprising a multiplicity of electrical conductors, a first one of said electrical conductors connecting said first electrical switch to a first of said electrical connections of said probe/system connector, and
   said ultrasound imaging system comprises:
   a beamformer for activating said ultrasound transducer array to transmit beams and forming vectors of acoustic data from receive signals transduced by said ultrasound transducer array following said beam transmits;

a display subsystem for displaying imaging data derived from said acoustic data;

first means for performing a first predetermined function on a set of said imaging data;

a sensor comprising a detecting circuit and a first input terminal connecting said detecting circuit to said first electrical connection of said probe/system connector, said detecting circuit outputting a first control signal in response to detecting a transition of said electrical switch from said first state to said second state; and a computer programmed to activate and control said first means to perform said first predetermined function in response to said first control signal.

8. The system as recited in claim 7, wherein said first predetermined function is freezing an image currently being displayed by said display subsystem.

9. The system as recited in claim 7, wherein said switch mechanism is further movable between said first position and a third position; said probe further comprises a second electrical switch operatively coupled to said switch mechanism, said second electrical switch having a first state when said switch mechanism is in said first position and a second state when said switch mechanism is in said third position, a second of said electrical conductors of said cable being connected to said second electrical switch; said ultrasound imaging system further comprising second means for performing a second predetermined function on said set of said imaging data, said sensor further comprises a second input terminal connecting said detecting circuit to said second electrical connection of said probe/system connector, said detecting circuit outputting a second control signal in response to detecting a transition of said second electrical switch from said first state to said second state, and said computer being programmed to activate and control said second means to perform said second predetermined function in response to said second control signal.

10. The system as recited in claim 9, further comprising a printer for printing said imaging data, wherein said second predetermined function is printing a copy of an image currently being displayed by said display subsystem.

11. A system comprising:

an ultrasound transducer probe comprising an array of piezoelectric transducer elements, a user-operable switch operable to transition between first and second states, and respective electrical conduction paths electrically connected to said piezoelectric transducer elements and to said user-operable switch; and an ultrasound imaging system comprising:
a transmit beamformer for pulsing said transducer array to transmit ultrasound beams;
a receive beamformer for forming receive beams of acoustic data derived from echo signals detected by the transducer array subsequent to said beam transmits;
a signal processing chain for converting said acoustic data into imaging data;
a display monitor for displaying said imaging data;
means for performing a function on said imaging data;
a sensor electrically connected to that electrical conduction path which is electrically connected to said user-operable switch, said sensor outputting a control signal in response to a transition from said first state to said second state of said user-operable switch; and a computer programmed to activate and control said means to perform said function in response to said control signal.

12. The system as recited in claim 11; wherein said function is freezing an image currently being displayed on said display monitor.

13. The system as recited in claim 11, further comprising a cine memory for storing imaging data, wherein said function is storing in said cine memory imaging data corresponding to an image currently being displayed on said display monitor.

14. The system as recited in claim 11, further comprising a printer for printing said imaging data, wherein said function is printing a copy of an image currently being displayed on said display monitor.

15. The system as recited in claim 11, wherein said user-operable switch comprises:

a switch mechanism movable relative to said probe housing between first and second positions;

a first electrical switch operatively coupled to said switch mechanism, said first electrical switch having an first state when said switch mechanism is in said first position and a second state when said switch mechanism is in said second position.

16. A system comprising:

an ultrasound transducer probe comprising an array of piezoelectric transducer elements and a user-operable switch operable to transition between first and second states; and an ultrasound imaging system comprising:
a transmitter for pulsing said transducer array to transmit ultrasound beams;
a receiver for acquiring acoustic data derived from echo signals detected by the transducer array subsequent to said beam transmits;
a signal processing chain for converting said acoustic data into imaging data in accordance with operating parameter settings;
a display device for displaying images representing said imaging data; and
a controller for setting an operating parameter of said ultrasound imagine system in response to a transition from said first state to said second state of said user-operable switch.

17. A system comprising:

an ultrasound transducer probe comprising an array of piezoelectric transducer elements and a user-operable input device operable to transition between first and second states; and an ultrasound imaging system comprising:
a transmitter for pulsing said transducer array to transmit ultrasound beams;
a receiver for acquiring acoustic data derived from echo signals detected by the transducer array subsequent to said beam transmits;
a signal processing chain for converting said acoustic data into imaging data in accordance with operating parameter settings;
a display device for displaying images representing said imaging data; and
a controller for changing an operating parameter of said ultrasound imaging system in response to a transition from said first state to said second state of said user-operable input device.

18. The system as recited in claim 17, wherein said operating parameter is receiver gain.

19. The system as recited in claim 17, wherein said operating parameter is dynamic range.

20. The system as recited in claim 17, wherein said operating parameter is a Doppler velocity scale.

21. A method for operating an ultrasound imaging system having a hand-held transducer probe, comprising the steps of:

holding the transducer probe;

placing the remote end of the transducer probe in acoustically coupled relationship with the body being examined;

viewing a first succession of images on a display screen while moving the transducer probe across the body, said first succession of images being produced while an operating parameter of the ultrasound imaging system is set at a first value;

operating a switch on the transducer probe to change the setting of said operating parameter of said ultrasound imaging system from said first value to a second value different than said first value; and viewing a second succession of images on the display screen while moving the transducer probe across the body, said second succession of images being produced while said operating parameter of the ultrasound imaging system is set at said second value.

\* \* \* \* \*